(12) United States Patent
Venon (10) Patent No.: US 8,692,774 B2
(45) Date of Patent: Apr. 8, 2014

(54) VIRTUAL COLONOSCOPY NAVIGATION METHODS USING A MOBILE DEVICE

(75) Inventor: Medhi Venon, Whitefish Bay, WI (US)

(73) Assignee: General Electric Company, Schenectady, NY (US)

(*) Notice: Subject to any disclaimer, the term of this patent is extended or adjusted under 35 U.S.C. 154(b) by 794 days.

(21) Appl. No.: 12/625,265

(22) Filed: Nov. 24, 2009

(65) Prior Publication Data

US 2011/0122068 A1    May 26, 2011

(51) Int. Cl.
*G06F 3/02* (2006.01)
*G09G 5/00* (2006.01)
*G06F 3/041* (2006.01)

(52) U.S. Cl.
USPC .......................................... 345/169; 345/173

(58) Field of Classification Search
None
See application file for complete search history.

(56) References Cited

U.S. PATENT DOCUMENTS

| 5,920,319 | A | 7/1999 | Vining et al. | |
|---|---|---|---|---|
| 7,149,564 | B2 | 12/2006 | Vining et al. | |
| 2003/0132936 | A1* | 7/2003 | Kreeger et al. | 345/420 |
| 2006/0007188 | A1* | 1/2006 | Reiner | 345/179 |
| 2006/0023966 | A1* | 2/2006 | Vining | 382/260 |
| 2006/0197753 | A1* | 9/2006 | Hotelling | 345/173 |

* cited by examiner

*Primary Examiner* — Nicholas Lee
(74) *Attorney, Agent, or Firm* — Hanley, Flight and Zimmerman, LLC (57) ABSTRACT

Certain examples provide systems and methods for mobile virtual colonoscopy. Certain examples provide a mobile device configured to view clinical content. The mobile device includes a data storage to store data including images for a virtual colonoscopy; a user interface to display the images for user viewing and manipulation; and a motion detector to capture movement of the mobile device with respect to a reference plane and to provide movement data. The mobile device includes a processor to receive input via the user interface and provide content, including the images, to the user interface. The processor is to provide a virtual colonoscopy using the images to a user via the user interface. The processor receives the movement data from the motion detector and translates the movement data to navigation commands in the virtual colonoscopy to allow the user to conduct a virtual colonoscopy using the mobile device.

17 Claims, 4 Drawing Sheets

FIG. 4

VIRTUAL COLONOSCOPY NAVIGATION METHODS USING A MOBILE DEVICE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

A virtual colonoscopy is a medical imaging procedure that uses x-ray image data in conjunction with a computer to produce two- and three-dimensional images of a patient's colon (large intestine) from the rectum to the lower end of the small intestine. Images are displayed to help diagnose colon and bowel disease, such as polyps, diverticulosis, and cancer. A virtual colonoscopy can be performed using computed tomography (CT) or with magnetic resonance imaging (MRI), for example.

Colorectal cancer is a leading cause of cancer death in the western world. Virtual colonoscopy is a new method for combined two-dimensional and three-dimensional imaging of the colon, using a multi-slice helical CT scanner, for example. This method has already demonstrated excellent results in polyp and cancer detection, having similar accuracy to Endoscopic colonoscopy in the detection of polyps above 6 millimeters in size. An application of this technique lies in diagnosing cases where conventional colonoscopy fails to demonstrate the entire colon due to technical problems. Another application is to investigate the colon proximal to an obstructing tumor, where both a barium enema and colonoscopy cannot overcome the obstruction. Virtual colonoscopy is also used for population screening.

Virtual colonoscopy has been tied to a radiologist's workstation. Using a thin client application, Web-based access can be possible from a laptop or workstation.

BRIEF SUMMARY

Certain embodiments of the present invention provide systems and methods for mobile virtual colonoscopy.

Certain examples provide a mobile medical computing system. The system includes a mobile device configured to view clinical content. The mobile device includes a data storage to store data including images for a virtual colonoscopy; a user interface to display the images for user viewing and manipulation; and a motion detector to capture movement of the mobile device with respect to a reference plane and to provide movement data. The mobile device also includes a processor to receive input via the user interface and provide content, including the images, to the user interface. The processor is to provide a virtual colonoscopy using the images to a user via the user interface. The processor receives the movement data from the motion detector and translates the movement data to navigation commands in the virtual colonoscopy to allow the user to conduct a virtual colonoscopy using the mobile device.

Certain examples provide a method for mobile virtual colonoscopy using a movement of a mobile device. The method includes loading a data set for a virtual colonoscopy at a mobile device; displaying, via a user interface at the mobile device, the images for user viewing and manipulation in a virtual colonoscopy; and capturing, using a motion detector in the mobile device, movement of the mobile device with respect to a reference plane to provide movement data for the mobile device. The method also includes conducting, using a processor, navigation of the virtual colonoscopy based on the movement data provided by the motion detector. The processor translates the movement data to navigation commands in the virtual colonoscopy to allow the user to conduct a virtual colonoscopy using the mobile device.

Certain examples provide a computer-readable storage medium having a set of instructions stored thereon which, when executed, instruct a processor to implement a method for mobile virtual colonoscopy using a movement of a mobile device. The method includes loading images for a virtual colonoscopy at a mobile device; displaying, via a user interface at the mobile device, the images for user viewing and manipulation in a virtual colonoscopy; and capturing, using a motion detector in the mobile device, movement of the mobile device with respect to a reference plane to provide movement data for the mobile device. The method also includes conducting, using a processor, navigation of the virtual colonoscopy based on the movement data provided by the motion detector. The processor translates the movement data to navigation commands in the virtual colonoscopy to allow the user to conduct a virtual colonoscopy using the mobile device.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Certain examples provide a mobile device offering virtual colonoscopy navigation, visualization, and analysis. Certain examples provide an ability to navigate, mark and perform the initial report of the virtual colonoscopy procedure without being close to a computer. Certain examples provide mobility and integration of multi-user sources as well as integration of navigation and annotation mechanisms into a single portable device.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, etc. storing the software and/or firmware.

In certain examples, a mobile device allows a user to display and interact with medical content stored on one or more clinical systems via the mobile handheld device. Without user interaction via a pointing device or button selection, a user can manipulate content, access different content, and collaborate with other users to analyze and report on exams and other medical content. A change in device orientation and/or position results in a change in device mode and set of available tools without closing or losing the patient context and previous screen(s) of patient information. Images can be manipulated, annotated, highlighted, and measured via the device. Enterprise functionality and real-time collaboration are provided such that the user can collaborate on a document in real time with other users as well as access content from systems such as a RIS, PACS, EMR, etc., and make changes via the mobile device.

The mobile device can display and interact with medical content via a plurality of modes. Each mode includes different content and associated tools. Each of the plurality of modes is accessible based on a change in orientation and/or position of the device while maintaining a patient context across modes. The mobile device also includes medical content analysis capability for display, manipulation, and annotation of medical content and real-time sharing of the content for user collaboration using multi-touch control by the user. The mobile device communicates with one or more clinical systems to access and modify information from the one or more clinical systems in substantially real-time.

The mobile device can be used to facilitate user workflow. For example, the mobile device uses an accelerometer and/or global positioning sensor and/or other positional/motion indicator to allow a user to navigate through different screens of patient content and functionality. The mobile device removes the requirement of using a user interface control to select between different screens. For example, multi-touch capability is provided to manipulate and modify content. Using multi-touch, a user can draw shapes and annotate to generate measurements, highlight abnormal structure, and/or add textual comments to an image, for example. Via the mobile device, a user can input and/or manipulate without adding external input devices. The position and motion sensor (s) are used to manipulate the navigation direction in the colonoscopy and/or the navigation speed, for example.

In certain examples, the mobile device provides enhance resetability for the user. For example, the device can undo, erase, and/or reset end user changes to default setting by tracking a device's position and/or orientation and responding to changes to the position/orientation. The device can undo and restart without additional user interface control input. The device can adjust a threshold parameter through user feedback, for example (e.g., a current setting may be too sensitive to normal movement of the device when carried or held by a user).

Certain examples integrate enterprise functions into a mobile device. For example, functionality such as a directory, calendar, geographic location, phone services, text message, email, etc., can be provided via the mobile device. Clinical information from various sources such as PACS, HIS, RIS, EMR, etc., can be provided via the mobile device. The mobile device interface can facilitate real-time collaboration with other end users. Information sharing and recording can be facilitated using multiple media services in real-time or substantially real-time, for example. The mobile device allows the user to focus on patient information and analysis while collaborating with one or more end users without switching or leaving the clinical context being reviewed, as well as exchanging medical data without losing the current state of the clinical context, for example. The mobile device provides a unified communication/collaboration point that can query and access information throughout different information systems, for example.

Certain examples facilitate user authentication via the mobile device. For example, the mobile device can authenticate a user's access to sensitive and/or private information. In certain embodiments, user authentication at the mobile device does not require the user to enter an identifier and password. Instead, the user is known, and the mobile device verifies if the current user is authorized for the particular content/application. Authentication is based on a unique identification number for the device, a connectivity parameter, and a PIN number for the user to enter, for example.

In some examples, the mobile device is used as a navigation and visualization device to conduct a virtual colonoscopy. A touch screen on the mobile device is used to mark qualitative and/or quantitative annotations during analysis. Additionally, using the mobile device, a user can replay the performed procedure as a playback function. A referring physician and/or the patient can see annotation(s), audio and/or text commentary(ies), etc., of reviewing radiologists from the same and/or a different mobile device, for example.

While preparations for a virtual colonoscopy (VC) can vary, a patient will usually be asked to take laxatives or other oral agents at home the day before the procedure to clear stool from the colon. A suppository is also used to cleanse the rectum of any remaining fecal matter. The patient is also given a solution designed to coat any residual faeces which may not have been cleared by the laxative. This is sometimes referred to as 'faecal tagging'. This allows the user (usually a consultant radiologist) viewing the three-dimensional (3D) images to effectively subtract the left over faeces, which may otherwise give false positive results.

A VC takes place in the radiology department of a hospital or medical center, for example. The examination takes about ten minutes and does not require sedatives. During the procedure, the patient is placed in a supine position on the examination table. A thin tube is inserted into the rectum so that air can be pumped through the tube in order to inflate the colon for better viewing. The examination table moves through an imaging scanner (e.g., a CT or MRI scanner) to produce a series of two-dimensional cross-sectional images along the length of the colon. The patient is asked to hold his/her breath during the scan to avoid distortion on the images. The scan is then repeated with the patient lying in a prone position. A computer program combines the obtained two-dimensional images to create a three-dimensional picture that can be viewed on a display and/or otherwise manipulated, for example.

After the examination, the images produced by the scanner are processed into a 3D image. A fly through capability (e.g., a cine program that allows the user move through the bowel as if performing a normal colonoscopy) can also be provided. A radiologist evaluates the results to identify any abnormalities. The patient may resume normal activity after the procedure, but if abnormalities are found and the patient needs conventional colonoscopy, it may be performed the same day.

Figure 1:
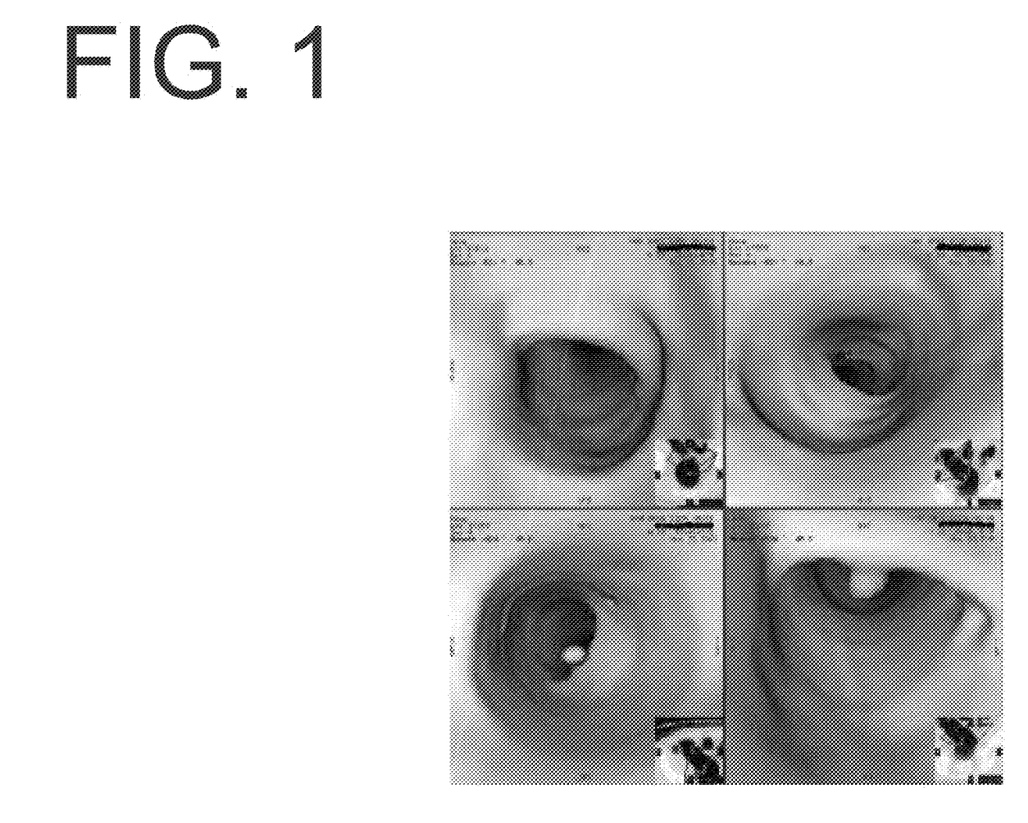
FIG. 1 illustrates example virtual colonoscopy images.

A VC is more comfortable than conventional colonoscopy for some people because it does not use a colonoscope. As a result, no sedation is needed, and the patient can return to his/her usual activities or go home after the procedure without the aid of another person. As shown, for example, in FIG. 1, a VC provides clearer, more detailed images than a conventional x-ray using a barium enema, sometimes called a lower gastrointestinal (GI) series. Further, about one in ten patients will not have a complete right colon (cecum) evaluation completed with conventional colonoscopy. A VC also takes less time than either a conventional colonoscopy or a lower gastrointestinal (GI) series. A VC provides a secondary benefit of revealing diseases or abnormalities outside the colon.

A mobile VC application allows a radiologist to perform the virtual colonoscopy anywhere with a handheld device including an embedded device to allow a spatial navigation within the colon. The handheld device allows a user to navigate, mark, and draft an initial report of the virtual colonoscopy procedure without being near a workstation computer. A physician can review the procedure and findings with the patient and with the referring physician and/or specialist with access anywhere. A mobile VC application allows the physician to review radiologist reading and outcomes with the patient by replaying the navigation mode and/or stepping to the radiologist key findings, for example.

In some examples, a user is provided with an ability to share findings and a walk-through of the findings using a smartphone (e.g., BlackBerry™, iPhone™, etc.) or other handheld device such as an iPod. Doctors can discuss the findings with the patient by replaying the reading, for example. In some examples, a user is provided with an ability to have a second opinion on the findings from a specialist and/or another radiologist without being in proximity to a workstation. The reading radiologist can contact a specialist for a second opinion and to provide feedback (e.g., commentaries and/or annotations) on the same procedures. The first physician can review and acknowledge or edit (e.g., a document review with tracking changes) the second radiologist's annotation. In some examples, a user is provided with an ability for the radiologist to schedule the VC procedure based on workload without physically being close to the reading workstation.

Using the mobile device, a user can access images to perform a VC at any location. For example, a radiologist can perform an emergency VC and/or critical reading remotely. Additionally, collaboration between the radiologist and a specialist and/or other radiologist can be facilitated via the mobile device to ensure accurate and faster diagnostics. Use of the mobile device can help increase the productivity of radiologists with better management of incoming request(s) through a worklist between "primary reading" and seeking an opinion. The mobile device enables use of the VC output of a multi-user document where radiologist, physician, and/or patient questions and findings can be combined.

Figure 2:
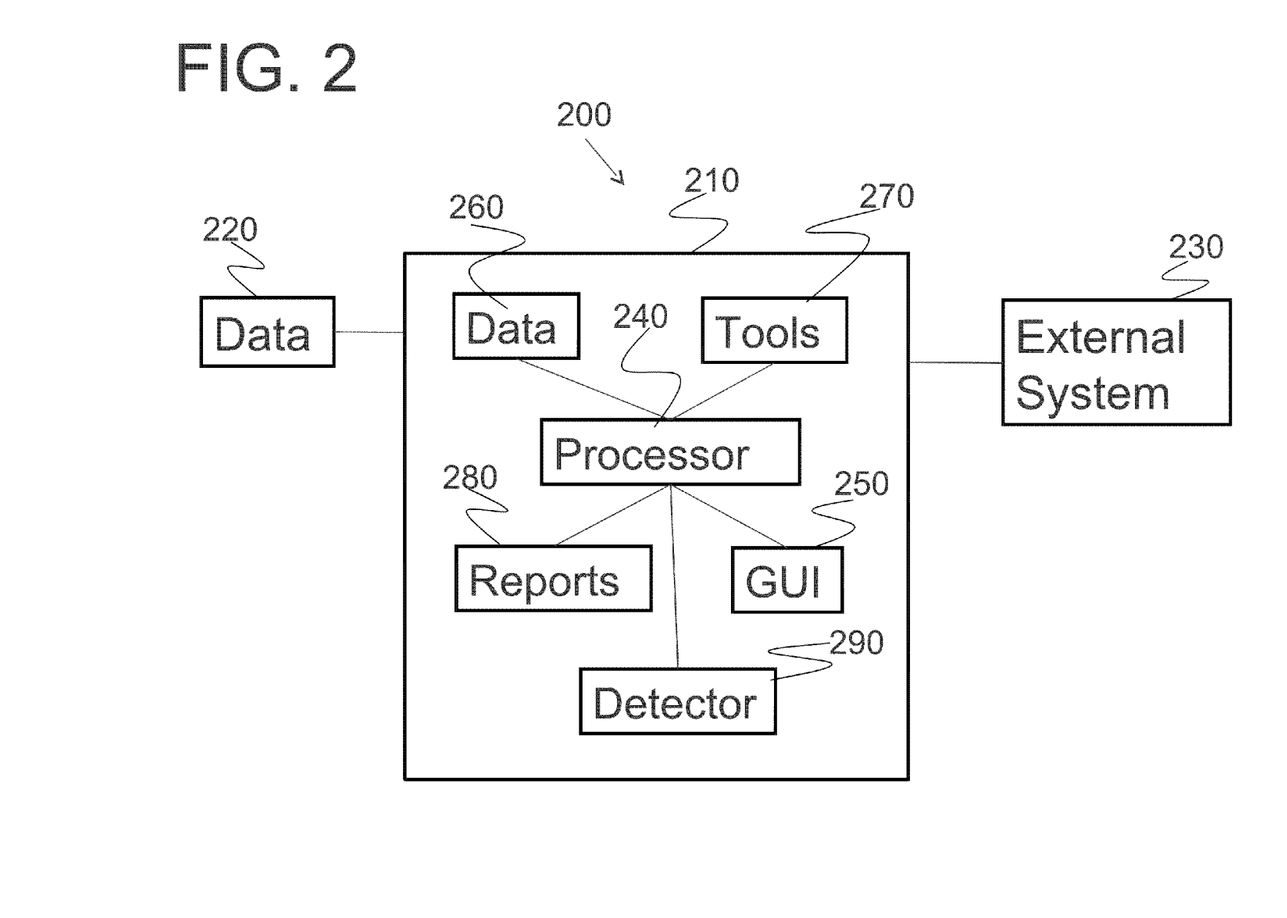
FIG. 2 depicts an example mobile virtual colonoscopy system including a mobile device and an external data store.

FIG. 2 depicts an example mobile VC system 200 including a mobile device 210, an external data source 220, and an external system 230. In some examples, the external data source 220 and external system 230 can be implemented in a single system. In some examples, a plurality of data sources 220 and/or external systems 230 can communicate with the mobile device 210. In some examples, a plurality of mobile devices 210 can communicate with one or more data sources 220 and/or external systems 230.

The data source 220 can provide images and/or other data to the mobile device 210 for VC and/or other application(s). In some examples, the data source 220 can also receive VC results, reports, and/or other information from the mobile device 210. The external system 230 can receive VC results, reports, and/or other information from the mobile device 210, for example. In some examples, the external system 230 can also provide images and/or other data to the mobile device 210. The data source 220 and/or external system 230 can be implemented using a system such as a PACS, RIS, HIS, CVIS, EMR, archive, data warehouse, imaging modality (e.g., x-ray, CT, MR, ultrasound, nuclear imaging, etc.).

The mobile device 210 can be implemented using a smart phone (e.g., BlackBerry™, iPhone™, etc.), Mobile Internet device (MID), personal digital assistant, cellular phone, handheld computer, etc. The mobile device 210 includes a processor 240 retrieving data, executing functionality, and storing data at the mobile device 210, data source 220, and/or external system 230. The processor 240 drives a graphical user interface (GUI) 250 providing information and functionality to a user and receiving user input to control the device 210, edit information, etc. The GUI 250 can include a touch pad/screen integrated with and/or attached to the device 210, for example. The mobile device 210 includes one or more internal memories and/or other data stores including data 260 and tools 270. Data storage can include any of a variety of internal and/or external memory, disk, Bluetooth remote storage communicating with the mobile device 210, etc. Using user input received via the GUI 250 as well as information and/or functionality from the data 260 and/or tools 270, the processor can generate one or more reports 280 related to the VC and/or other activity at the mobile device 210, for example. A detector 290, such as an accelerometer, position encoder (e.g., absolute, incremental, optical, analog, digital, etc.), global positioning sensor, and/or other sensor, etc., can be used to detect motion of the mobile device 210 (e.g., shaking, rotating or twisting, left/right turn, forward/backward motion, etc.). Detected motion can be used to affect operation and/or outcomes at the mobile device 210. For example, motion can be used to navigate through a VC using the mobile device 210. Motion detected by the detector 290 can be relayed to the processor 240 to provide corresponding movement in the displayed VC, for example. The processor 240 can include and/or communicate with a communication interface component to query, retrieve, and/or transmit data to and/or from a remote device, for example.

In operation, for example, the mobile device 210 requests (and/or receives via a push rather than pull model) one or more data sets (e.g., images and optionally associated data such as annotations including but not limited to structured reporting) from the data source 220 for a virtual colonoscopy. Using a VC navigation tool available on the mobile device 210, a user can activate a VC on the mobile device 210 using the images (and optionally associated data). The data 260 and tools 270 on the mobile device 210 facilitate user navigation, annotation, editing, and/or reporting (e.g., report(s) 280) via the mobile device 210. Motion detected by the detector 290 facilitates user navigation through the VC images. The motion detector 290 translates the detected motion into movement data that can be used by the processor 240. For example, left motion of the device 210 translates into a left navigation in the VC. Right motion of the device 210 translates into a right navigation in the VC. Forward motion of the device 210 translates to forward navigation in the VC. Backward motion of the mobile device 210 translates to backward navigation in the VC. In some examples, a default translation between detected device 210 movement is provided. In some examples, a user and/or application can customize one or movement translations. Output from the VC (e.g., a report 280) can be transmitted to the external system 230 via a communication interface on the mobile device 210.

Figure 3:
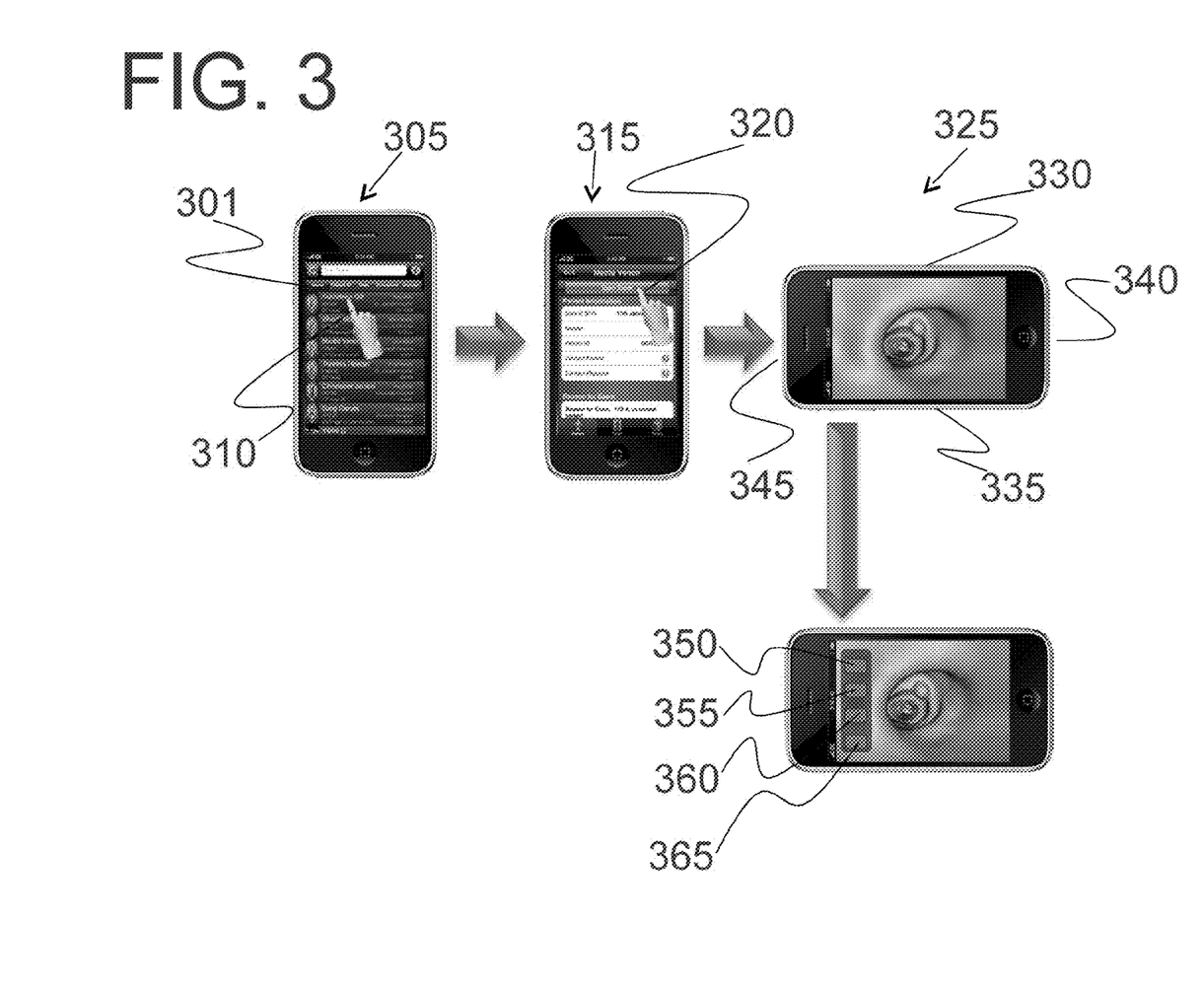
FIG. 3 illustrates an example virtual colonoscopy application workflow using a mobile device.

FIG. 3 illustrates an example VC application workflow using a mobile device. FIG. 3 depicts a user perspective of mobile device manipulation and feature availability for VC and/or other application workflow. At 305, a user 310 is selected from a patient worklist on the mobile device 301. At 315, an exam 320 is selected.

Once the VC exam 320 is opened, at 325, the mobile device 301 can be used to navigate through the VC. For example, moving the device 301 left 330 initiates a left turn in VC motion through the exam 320. Moving the device 301 right 335 initiates a right turn in VC motion through the exam 320. Moving the device 301 forward 340 or backward 345 triggers a corresponding forward or backward navigating motion in the VC exam 320.

In addition to navigating the VC through movement of the device 301, the mobile device 301 can be used for one or more functions such as editing, annotation, dictation, etc. For example, a user can touch the user interface screen of the mobile device 301 to annotate a region of interest (e.g., a polyp). A user can perform a multi-touch action on the user interface screen of the mobile device 301 to request a distance measurement, for example. A user can touch the user interface screen in conjunction with the activation of audio functionality to provide comments regarding the VC.

The mobile device 301 can include functionality to allow a user to edit 350, play back 355, review 360, and/or share 365 VC image and/or other data content, for example. Using edit 350, a user can add an "audio" and/or text comment after marking a region of an image. Using play back 355, a user can play back an existing VC with marker(s) and attachment(s). Play back 355 can include an ability to pause, play, rewind, touch a marker to listen to and/or display content, etc. The review 360 allows a user to review one or more comments from others to validate and/or invalidate the comment. Using share 365, a user can share the VC and the finding(s) and/or marker(s) with other user(s).

Mobile devices (including but not limited to a smart phone (e.g., BlackBerry™ iPhone™, etc.), laptop, personal digital assistant, cellular phone, handheld computer, etc.) follow standards and protocols that mandate a description or identifier for the communicating component (including but not limited to a network device MAC address, a phone number, a GSM phone serial number, an International Mobile Equipment Identifier, and/or other device identifying feature). These identifiers can fulfill a security requirement for device authentication. The identifier is used in combination with a front-end user interface component that leverages a multi-touch input device such as but not limited to; Personal Identification Number, Keyword, Drawing/Writing a signature (including but not limited to; a textual drawing, drawing a symbol, drawing a pattern, performing a gesture, etc.), etc., to provide a quick, natural, and intuitive method of authentication. Feedback can be provided to the user regarding successful/unsuccessful authentication through display of animation effects on a mobile device user interface. For example, the device can produce a shaking of the screen when user authentication fails. Security standards, virtual private network access, encryption, etc., can be used to maintain a secure connection.

For example, an end user launches a secure application (including but not limited to a clinical application requiring a degree of security). The application reads the unique identifying features of the device and perform an authentication "hand-shake" with the server or data-providing system. This process is automated with no user input or interaction required. After the device has been authenticated, the user is presented with an application/user level authentication screen (including but not limited to a personal identification number (PIN), password/passcode, gesture, etc.) to identify to the application that the user is indeed a valid user. This feature functions as a method to provide device level security as well as an ability to lock the device (e.g., if the user wishes to temporary lock the device but not logout/shutdown the application), for example.

In certain embodiments, mobile devices, such as but not limited to smart phones, ultra mobile and compact notebook computers, personal digital assistants, etc., offer many applications aside from phone functions. Certain embodiments allow clinical end users to enhance their collaboration with their colleagues, patients, and hospital enterprise via the mobile device.

By integrating enterprise functions for mobile devices, such as but not limited to a directory, calendar, geographic location, phone services, text messages, email services, etc., with clinical information from various clinical sources, such as but not limited to PACS, HIS, RIS, etc., end users can access patient centric information and enable real-time or substantially real-time collaboration with other end users to collaborate on a specific patient case. The collaboration allows information sharing and recording using multiple media services in real-time or substantially real-time.

Collaboration leverages global positioning system, multi-touch capability, high resolution displays, etc., in mobile devices within small form factors, for example. Using the mobile device, the end user can focus on patient information analysis while collaborating with one or many other end users without switching or leaving the clinical context being reviewed. It allows exchanging medical data without losing the current state of the clinical context. It also leverages all the multi-media features of a device from healthcare applications. For example, clinical and non-clinical information can be provided to aid a clinical user, such as a physician, nurse, technologist, administrator, etc., in patient care and workflow decisions. The mobile device provides the user with an ability to locate and contact another user (including but not limited to a patient, referring physician, surgeon, pharmacy, emergency patient contact, etc.). The mobile device provides an ability to locate and provide directions with a map to an address of another user, department, or institution (including but not limited to a home address, business address, drug store, hospital clinic, hospital remote facility, specialized clinical facility, etc.). Using a contact address and current location determined by a built-in global positioning feature, a map and guide route can be generated to the destination. This feature also allows relatively accurate time estimates for travel to reach a destination. The mobile device provides an ability to locate and contact another user involved in a patient's care by navigating a user interface that provides contact information of other users involved in the patient's care. Communication is then initiated (including but not limited to by phone, SMS, text messaging, email services, etc.) to collaborate on a patient's exam/case/care. Other users can be included as needed by using the interface (including but not limited to a multi-touch user interface) to search through a contact list (including but not limited to a local contact list, enterprise contact list, clinical context contact list, etc.). Clinical information can then be conveyed to collaborators through a variety of communication methods (including but not limited to phone, SMS, text messaging, email services, etc.) and added to the patient's care record (including but not limited to Clinical Report, Audit Tracking, etc.). Navigation through this information is provided by a user interface that accepts multi-touch user input, for example.

Figure 4:
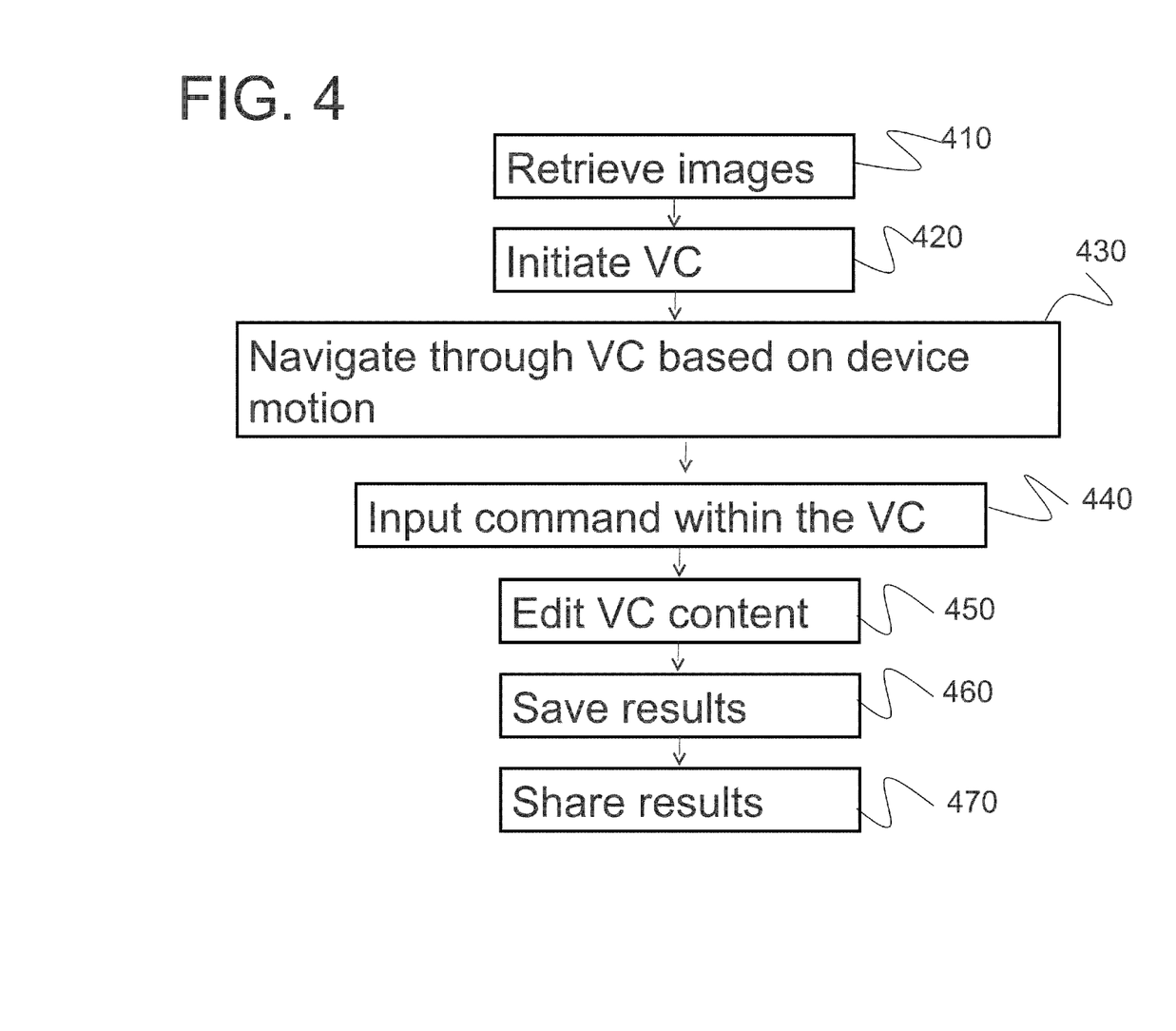
FIG. 4 illustrates a flow diagram for a method for virtual colonoscopy navigation using a mobile device.

FIG. 4 illustrates a flow diagram for a method 400 for virtual colonoscopy navigation using a mobile device. At 410, images are retrieved from a data source to a mobile device. The data source can be internal and/or external to the mobile device. Images can be retrieved from a plurality of data sources, for example. At 420, a virtual colonoscopy is initiated on the mobile device. The VC can be initiated by selected one or more menu options and/or tools on a mobile device user interface via touch, stylus contact, key/button press, voice command, and/or other selection, for example. A user can select a VC tool and/or can select the set of images to initiate the VC, for example.

At 430, navigation through a VC is facilitated based on motion of the mobile device. For example, the mobile device produces a left turn in VC motion based on user movement of the mobile device to the left. The movement of the mobile device can be an extended movement of the device to the user's left and/or a quick turn or tilt of the mobile device to the left, for example. Similarly, the mobile device produces a right turn in VC motion based on user movement of the mobile device to the right. The mobile device provides forward navigation in the VC based on user movement of the mobile device in a forward direction away from the user, for example. The mobile device provides backward navigation in the VC based on user movement of the mobile device in a backward direction toward the user, for example.

At 440, one or more commands are processed for VC at the mobile device. For example, in addition to navigating the VC through movement of the mobile device, the mobile device can be used for one or more functions such as editing, annotation, dictation, etc. For example, a user can touch the user interface screen of the mobile device to annotate a region of interest (e.g., a polyp). A user can perform a multi-touch action on the graphical user interface of the mobile device to request a distance measurement, for example. A user can touch the user interface screen in conjunction with the activation of audio functionality to provide comments regarding the VC, for example. Using play back, a user can play back an existing VC with marker(s) and attachment(s), for example. Play back can include an ability to pause, play, rewind, touch a marker to listen to and/or display content, etc. Review allows a user to review one or more comments from others to validate and/or invalidate the comment, for example. A 450, the mobile device facilitates user editing of VC content. Using edit, a user can add an "audio" and/or text comment after marking a region of an image, for example.

At 460, VC results can be saved. For example, progress and/or status within a VC can be saved to allow a user to resume navigation later. Alternatively or in addition, annotations, comments, reports, and/or other attachments can be saved at the mobile device and/or an external system for further use and/or later retrieval, for example. At 470, VC results can be shared. Using share, a user can share the VC and the finding(s) and/or marker(s) with other user(s), for example. Sharing can be facilitated via electronic mail, facsimile, messaging, telephonic transmission, saving at an external system, etc., from the mobile device, for example.

As described herein, the method 400 can be implemented using the mobile device in one or more combinations of hardware, software, and/or firmware, for example. The method 400 can operate with the mobile device in conjunction with one or more external systems (e.g., data sources, healthcare information systems (RIS, PACS, CVIS, HIS, etc.), archives, imaging modalities, etc.). One or more components of the method 400 can be reordered, eliminated, and/or repeated based on a particular implementation, for example.

Thus, certain examples provide mobile health solutions for a virtual colonoscopy workflow. Certain examples provide systems and methods for intuitive image annotation, editing, and reporting. Certain examples enable easy to use text annotation and reports for mobile VC and/or other clinical solutions. Certain examples provide a technical effect of navigating, reviewing, editing, and sharing a VC via a mobile device without the need for a workstation.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A mobile medical computing system, the system comprising:
    a mobile device configured to view clinical content, the mobile device comprising:
        a data storage to store data including images for a virtual colonoscopy;
        a user interface to display the images for user viewing and manipulation;
        a motion detector to capture movement of the mobile device with respect to a reference plane to provide movement data from the movement of the mobile device with respect to the reference plane;
        a processor to receive input via the user interface and provide content, including the images, to the user interface, the processor to provide a virtual colonoscopy using the images to a user via the user interface, the processor to receive the movement data from the motion detector and translate the movement data to navigation commands in the virtual colonoscopy to allow the user to conduct a virtual colonoscopy using the mobile device, the processor to translate input received from the user interface into annotation of results of the virtual colonoscopy, the processor to facilitate generation of a report of the virtual colonoscopy procedure via the mobile device, the processor to provide a mobile review of the virtual colonoscopy by user edit, replay, and sharing of the virtual colonoscopy and identified findings via the user interface.

2. The system of claim 1, wherein the processor is to include a default translation from the movement data to navigation commands.

3. The system of claim 2, wherein the default translation is customizable by a user.

4. The system of claim 1, wherein the user interface comprises a touch screen interface.

5. The system of claim 4, wherein the images can be manipulated, annotated, and measured via the user interface.

6. The system of claim 4, wherein the user interface and the processor support multi-touch recognition, wherein, using at least one of multi-touch or keypad buttons, a user can draw shapes and annotate to generate measurements, highlight abnormal structure, and add textual comments to an image.

7. The system of claim 1, wherein the motion detector comprises an accelerometer detecting motion of the device and allowing a user to navigate through the virtual colonoscopy images based on the detected movement data.

8. A method for mobile virtual colonoscopy using a movement of a mobile device, the method comprising:
    loading images for a virtual colonoscopy at a mobile device;
    displaying, via a user interface at the mobile device, the images for user viewing and manipulation in a virtual colonoscopy;
    capturing, using a motion detector in the mobile device, movement of the mobile device with respect to a reference plane to provide movement data from the movement of the mobile device with respect to the reference plane;
    conducting, using a processor, navigation of the virtual colonoscopy based on the movement data provided by the motion detector, the processor translating the movement data to navigation commands in the virtual colonoscopy to allow the user to conduct a virtual colonoscopy using the mobile device;
    translating input received from the user interface into annotation of results of the virtual colonoscopy;
    facilitating generation of a report of the virtual colonoscopy procedure via the mobile device; and
    facilitating a mobile review of the virtual colonoscopy by user edit, replay, and sharing of the virtual colonoscopy and identified findings via the user interface.

9. The method of claim 8, wherein the processor is to include a default translation from the movement data to navigation commands.

10. The method of claim 9, wherein the default translation is customizable by a user.

11. The method of claim 8, wherein the user interface comprises a touch screen interface.

12. The method of claim 11, further comprising manipulating, annotating, and measuring an image in the virtual colonoscopy via the user interface.

13. The method of claim 11, further comprising accepting multi-touch user input to draw shapes and annotate to generate measurements, highlight abnormal structure, and add textual comments to an image in the virtual colonoscopy.

14. The method of claim 8, wherein the motion detector comprises an accelerometer detecting motion of the device and allowing a user to navigate through the virtual colonoscopy images based on the detected movement data.

15. A tangible computer-readable storage medium having a set of instructions stored thereon which, when executed, instruct a processor to implement a method for mobile virtual colonoscopy using a movement of a mobile device, the method comprising:
    loading images for a virtual colonoscopy at a mobile device;
    displaying, via a user interface at the mobile device, the images for user viewing and manipulation in a virtual colonoscopy;
    capturing, using a motion detector in the mobile device, movement of the mobile device with respect to a reference plane to provide movement data from the movement of the mobile device with respect to the reference plane;
    conducting, using a processor, navigation of the virtual colonoscopy based on the movement data provided by the motion detector, the processor translating the movement data to navigation commands in the virtual colonoscopy to allow the user to conduct a virtual colonoscopy using the mobile device;
    facilitating a mobile review of the virtual colonoscopy by user edit, replay, and sharing of the virtual colonoscopy and identified findings via the user interface; and
    accepting multi-touch user input to draw shapes and annotate to generate measurements, highlight abnormal structure, and add textual comments to an image in the virtual colonoscopy.

16. The computer-readable storage medium of claim 15, further comprising manipulating, annotating, and measuring an image in the virtual colonoscopy via the user interface, wherein the user interface is a touch screen user interface.

17. The computer-readable storage medium of claim 15, wherein the motion detector comprises an accelerometer detecting motion of the device and allowing a user to navigate through the virtual colonoscopy images based on the detected movement data.

* * * * *